United States Patent [19]
Hollister et al.

[11] Patent Number: 5,549,690
[45] Date of Patent: Aug. 27, 1996

[54] PROSTHETIC THUMB JOINT AND METHOD OF MANUFACTURE

[75] Inventors: Anne Hollister, Downey, Calif.; Mari S. Truman, Warsaw, Ind.; Leonard Bodell, Paradise Valley, Ariz.; Louise Focht, San Diego, Calif.

[73] Assignee: Avanta Orthopaedics, San Diego, Calif.

[21] Appl. No.: 202,910

[22] Filed: Feb. 28, 1994

Related U.S. Application Data

[63] Continuation-in-part of Ser. No. 169,297, Dec. 17, 1993.

[51] Int. Cl.$^6$ ........................................ A61F 2/42
[52] U.S. Cl. .............................. 623/21; 623/18; 623/901
[58] Field of Search ............................ 623/18, 20, 21, 623/901

[56] References Cited

U.S. PATENT DOCUMENTS

| | | |
|---|---|---|
| 4,021,864 | 5/1977 | Waugh ........................................ 623/21 |
| 4,156,944 | 7/1979 | Schreiber et al. ........................ 623/21 |
| 4,178,640 | 12/1979 | Buechler et al. . |
| 4,194,250 | 3/1980 | Walker ........................................ 623/18 |
| 4,229,841 | 10/1980 | Youm et al. . |
| 4,242,759 | 1/1981 | White .......................................... 623/21 |
| 4,349,922 | 9/1982 | Agee . |
| 4,822,365 | 4/1989 | Walker et al. ............................ 623/20 |
| 4,911,719 | 3/1990 | Merle ........................................ 623/18 |
| 4,944,758 | 7/1990 | Bekki et al. . |
| 4,955,916 | 9/1990 | Carignan et al. ........................ 623/21 |
| 4,959,071 | 9/1990 | Brown et al. . |
| 5,037,440 | 8/1991 | Koenig ........................................ 623/21 |
| 5,061,288 | 10/1991 | Berggren et al. ........................ 623/18 |
| 5,133,758 | 7/1992 | Hollister . |
| 5,326,364 | 9/1994 | Clift, Jr. et al. ........................ 623/21 |
| 5,405,400 | 4/1995 | Linscheid et al. ...................... 623/21 |
| 5,413,609 | 5/1995 | Nicol et al. .............................. 623/21 |

FOREIGN PATENT DOCUMENTS

| | | |
|---|---|---|
| 0350371 | 1/1990 | European Pat. Off. . |
| 2605878 | 5/1988 | France .................................... 623/21 |
| 2519865 | 11/1976 | Germany . |
| 2045085 | 10/1980 | United Kingdom . |
| 1582974 | 1/1981 | United Kingdom .................. 623/21 |

OTHER PUBLICATIONS

Brand et al., Clinical Mechanics of the Hand, pp. 35–39, 1985, Mosby Year Book.
Thompson et al., A Hand Biomechanics Workstation, pp. 335–343, Aug. 1988, Computer Graphics, vol. 22, No. 4.
Ateshian et al., Determination of Thumb Carpometacarpal Joint Contact in Lateral Pinch, Aug. 30–Sep. 4, 1990, First World Congress of Biomechanics.
Giurintano et al., Force Analysis of the Thumb for a Five–Link System, ASME 1991, AMD–vol. 120, 1991 Biomechanics Symposium.
Hollister et al., The Axes of Rotation of the Thumb Carpometacarpal Joint, Oct. 12, 1990–Dec. 3, 1991, Journal of Orthopaedic Research.
Hollister, et al., Off Set Hinges: A General Theory for Synovial Joint Kinematics; Undated, Department of Rehabilitation Research, Carville, LA 70721.

*Primary Examiner*—David Isabella
*Assistant Examiner*—Laura Fossum
*Attorney, Agent, or Firm*—Nydegger & Associates

[57] ABSTRACT

A method for modeling a prosthetic CMC thumb joint, and the joint manufactured therefrom, involves anatomically locating the two non-perpendicular and non-intersecting axes of rotation for the joint. The surface of revolution about these two axes, which is a torus, is then used to mathematically model the bearing surfaces of the prosthetic joint.

13 Claims, 4 Drawing Sheets

PROSTHETIC THUMB JOINT AND METHOD OF MANUFACTURE

This application is a continuation-in-part application of U.S. application Ser. No. 169,297 filed on Dec. 17, 1993.

FIELD OF THE INVENTION

The present invention pertains generally to prosthetic replacement joints. More particularly, the present invention pertains to two-member joints having members with respective corresponding surfaces that mate and move relative to each other for simultaneous rotation of the members about two separate axes of rotation. The present invention is particularly, but not exclusively, useful as a prosthetic joint for duplicating anatomical movement of a joint in the human skeleton.

BACKGROUND OF THE INVENTION

Nature has created many of the skeletal joints of the human anatomy such that the movement of one bone relative to the other bone, or bones, at the joint is best described as a rotational motion within a definable envelope. Specifically, the normal movement of a bone at a joint is a rotation of the bone about two different axes which are non-perpendicular and non-intersecting. Several mechanical advantages result from this fact. First, the kinematics of anatomical joints allows for more than just simple rotation in a plane. Specifically, because the two axes of rotation are non-perpendicular and non-intersecting, rotation of the bone about these two axes manifests rotations in all three anatomical planes (sagittal, transverse and coronal). Equally important, because only two axes of rotation are involved, anatomical joints require fewer muscles to achieve this rotation and maintain stability of a bone about the joint than would be required for a structure which uses three axes of rotation to achieve the same movement. Thus, anatomical joints are very mechanically efficient. The result of all this is what people perceive as normal skeletal movement.

Many prosthetic replacements for diseased or damaged joints have been developed and used over the years. Clearly, the intention in developing these joints has been to effectively duplicate the natural kinematics of the particular anatomical joint that is to be replaced. To do this, however, there has been no successful attempt to duplicate or mimic the natural boney structure of the joint. Instead, prosthetic joint designs have typically been driven by conventional considerations of joint movement relative to the anatomical reference planes. This has caused many to overlook the fact that normal bone movement about a joint can involve simultaneous interrelated movements in all of the reference planes. As a consequence of the conventional approaches used to design prosthetic replacement joints, the joints have been designed with either a single axis of rotation or with orthogonal axes of rotation. For example, U.S. Pat. No. 4,944,758, which issued to Bekki et al. for an invention entitled "Artificial Finger Joint", discloses a single axis joint which guides one member of the joint as it bends relative to the other joint member in a prescribed direction. As another example of conventionally designed prosthetic replacement joints, U.S. Pat. No. 4,229,841, which issued to Youm et al. for an invention entitled "Wrist Prosthesis", discloses a joint which provides for relative movement of the components about two substantially perpendicular axes. As an example of a three axes prosthesis, U.S. Pat. No. 4,349,922, which issued to Agee for and invention entitled "Joint Prosthesis with Improved Articulation Means", discloses a combination of linking pins which allows for members of the joint to pivot about three different axes. Unlike the above cited references which include interconnected members, U.S. Pat. No. 4,959,071, which issued to Brown et al. for an invention entitled "Partially Stabilized Knee Prosthesis", discloses a prosthetic joint which includes members that are not interconnected, but which rotatably slide relative to each other. Still, despite this distinction, the prosthetic joint disclosed by Brown et al. is restricted to rotation about a single axis.

None of the above cited references either teach or suggest designing a prosthetic replacement joint by first analyzing the kinematics of the joint itself. If this were done, the naturally occurring two non-perpendicular and non-intersecting axes of rotation, which are characteristic of a normal joint, would become evident. With this in mind, the present invention has recognized that the abutting surfaces of normal bones at a joint are surfaces of revolution. Specifically, each of the abutting surfaces of the bones at a joint is a surface of revolution about the joint's two non-perpendicular and non-intersecting anatomical axes of rotation. Further, the present invention recognizes that this surface of revolution is a torus, and specifically a skewed torus, which has parameters that can be geometrically varied to recreate the particular bone joint surface of interest. Using these observations, the present invention recognizes that the boney cartilaginous structures of an anatomical joint can be reproduced for a prosthesis and employed to restore normal joint kinematics.

It is interesting to note that the anatomical shapes of abutting bone surfaces at a joint have developed naturally to take advantage of a bone's capacity for carrying relatively large compressive forces. At the same time, these bone surface configurations minimize the transmission of torsional and shear forces which are not as well tolerated by boney structures as are compressive forces. As implied above, the naturally occurring configurations of abutting bone surfaces which achieve this force distribution can be characterized as surfaces of revolution about two non-perpendicular and non-intersecting axes.

The carpometacarpal (CMC) joint of the thumb is a case in point. Anatomically, the CMC joint establishes a rotational movement of the first metacarpal bone relative to the trapezium bone which is properly characterized as a mutual rotation about two off-set axes. It happens that one of these axes is located on the trapezium while the other is located on the first metacarpal bone. Interestingly, nature has provided the muscle network in the thumb which must effectively moves the respective bones at the CMC joint in rotation about these axes. Specifically, but without going into great anatomical detail, nature provides a pair of muscles for each off-set axis of the CMC joint. The individual muscles in each of these pair of muscles act opposite to each other to move the bones at the joint in rotation about the particular off-set axis with which they are associated. Thus, the complete natural movement of the thumb at the CMC joint is accomplished by only four muscles, which act in pairs. Further, nature uses these same muscles to move the other joints of the thumb, namely the metacarpal phalangeal (MP) and interphalangeal (IP) joints, which are distal to the CMC joint.

Prior attempts to create an effective replacement prosthesis for the CMC joint have typically relied on a ball and socket structure. These prosthesis moved about three perpendicular intersecting axes of rotation, and the placement of the axes of rotation relative to the thumb muscles and the external loads was not considered in their design. As indicated above, the thumb has only four muscles associated with the CMC joint. On the other hand, a ball and socket configuration would require six muscles, or three pairs, to effectively articulate the thumb about the axes of the joint. As we know, however, nature does not provide the needed extra pair of muscles which would be required for a three axis joint. Consequently, if a three axis joint is used, the need for additional muscle action upsets the balance of the entire thumb. Unfortunately, due to the interlinking involved, this imbalance is extended to include an adverse effect on operation of the MP and IP joints as well as the CMC joint.

An additional difficulty encountered in using a ball and socket type structure, as a CMC joint prosthesis is the inherent requirement for generous resection of the bones. Typically, straight cuts or hollowing out of the bone is necessary before such prosthesis can be attached to the trapezium and metacarpal bones of a CMC joint. Procedures using previously known CMC prosthesis joints have required removal of the trapezial joint surface, and in some instance the whole bone has been removed. Obviously, excessive resection or removal of bone is to be avoided.

The present invention recognizes that a prosthetic CMC joint can be manufactured and used which will effectively duplicate the anatomical structure of the joint. Further, the present invention recognizes that bone can be conserved by following a strategy which relies on resurfacing arthroplasty with limited, if any, bone resection requirements.

In light of the above it is an object of the present invention to provide a method for modeling a prosthetic joint which produces a prosthetic replacement joint which will restore normal joint kinematics. Another object of the present invention is to provide a method for modeling a prosthetic joint which produces a prosthetic replacement joint that maintains the mechanical advantage of the muscles which cross the joint. Still another object of the present invention is to provide a method for modeling a prosthetic joint which produces a prosthetic replacement joint which recreates the normal joint's axes of rotation. Yet another object of the present invention is to provide a method which can be employed for modeling different types of prosthetic replacement joints. Still another object of the present invention is to provide a prosthetic carpometacarpal joint that allows the stresses which act across the prosthesis to be dissipated over a large area of bone to increase the load bearing capability of the prosthesis and reduce the likelihood of failure of the prosthetic joint. It is another object of the present invention to provide a prosthetic carpometacarpal joint that allows for bone conservation by relying on bone surface replacement, rather than extensive bone resection or removal, in preparation for prosthesis attachment. Another object of the present invention is to provide a method for modeling prosthetic replacement joint which is relatively easy to accomplish and comparatively cost effective.

SUMMARY OF THE INVENTION

The prosthetic joint of the present invention, and its method of manufacture, pertains to a two-member joint which relies on the identification and location of two separate axes of rotation that will serve as the basic references from which anatomical movement of the joint is duplicated. Both of these axes, and their location relative to each other, are anatomically identifiable and are unique for the particular joint to be duplicated. One of the axes, the first axis, is anatomically referenced relative to one member of the joint. The other axis, the second axis, is also anatomically correct and is located with a predetermined relationship to the first axis. Typically, these axes of rotation are not perpendicular and do not intersect. Stated differently, the predetermined relationship between the first and second axis is characterized by a first off-set angle ($\alpha$), a second off-set angle ($\beta$), and the projected distance between the two axes.

As indicated above, the prosthetic joint of the present invention includes two members. A first member of the joint has a first surface which is generated mathematically as a surface of revolution about both the first axis and the second axis. A second member of the joint has a second surface which mates with the first surface of the first member. Through this relationship, the second member is able to rotate relative to the first member about both the first axis and the second axis.

The actual topography and shape of the first and second surfaces for the respective members of the joint are determined by the location of these interfacing surfaces relative to the first and second axes of rotation. For purposes of the present invention, the location of the interfacing first and second surfaces is determined anatomically. Depending on the particular joint to be duplicated, it can be either proximal to both axes, intermediate to the axes, or distal to both axes.

The range of motion of the joint is determined both by the shapes of the interfacing surfaces, and by the dimensions of these surfaces. More specifically, the range of motion is determined mathematically by the number of degrees of rotation desired about each axes of rotation. Further, insofar as dimensions are concerned, in order for members of the joint to remain in contact and effectively duplicate a normal anatomical range of motion, the surface of the first member could have an area which is larger than the surface area of the second member. The second member is then able to effectively rotate about both axes of rotation as its second surface moves over the first surface of the first member.

As intended for the present invention, for a joint replacement, one member of the prosthetic joint is attached and anchored to the proximal bone of the original joint. The other member of the joint is then attached and anchored to the distal bone, or bones, of the original joint. The members of the prosthetic joint are then juxtaposed at their respective rotational surfaces to kinematically duplicate the joint which needed to be replaced.

In the specific case of the CMC joint, the prosthesis comprises a trapezial member and a metacarpal member. According to the present invention the trapezial member has an engaging surface which is formed as a surface of revolution about two off-set axes. Specifically, for the CMC joint, one of theses off-set axes is located on the trapezium and the other is located on the first metacarpal bone. Thus, the surface of revolution for the CMC joint is located between the two axes.

Like the trapezial member, the metacarpal member of the CMC joint prosthesis has an engaging surface. Also like the trapezial member, the engaging surface of the metacarpal member is formed as a surface of revolution about the two off-set axes. The engaging surface of the metacarpal member, is specifically shaped for mating engagement with the engaging surface of the trapezial member.

The trapezial member of the prosthetic CMC joint of the present invention includes three pegs which extend from the member. As intended for the present invention, the three pegs on the trapezial member are substantially parallel to each other so that the member can be press-fitted into the prepared surface of the trapezium. Specifically, this is done with an orientation which presents the engaging surface of the trapezial member as an effective duplication of the anatomical surface of the trapezium. Further, it has been determined that stabilized fixation of the trapezial member can be enhanced by attaching one of the pegs to the trapezium near the volar beak. This is so because the cortical bone in this region is of good quality and will provide significant stability to the prosthesis-bone interface. Further, fixation of the trapezial member in this region will help the implant resist undesirable motion (dorso-radial migration) at the bone interface.

Somewhat different from the peg arrangement for the trapezial member, the metacarpal member of the CMC joint includes a stem which extends from the member. The stem is substantially triangular in its cross-section, and it is slightly bent to correspond to the anatomical shape of the metacarpal canal. With this configuration, the stem of the metacarpal member is insertable into the proximal canal of the first metacarpal bone to anchor the metacarpal member into a position and orientation for mating engagement with the trapezial member. As intended for the present invention, once the trapezial member and the metacarpal member have been properly anchored to their respective trapezium and first metacarpal bone, the muscles and ligaments of the thumb are used to hold the respective members in their intended mating engagement.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
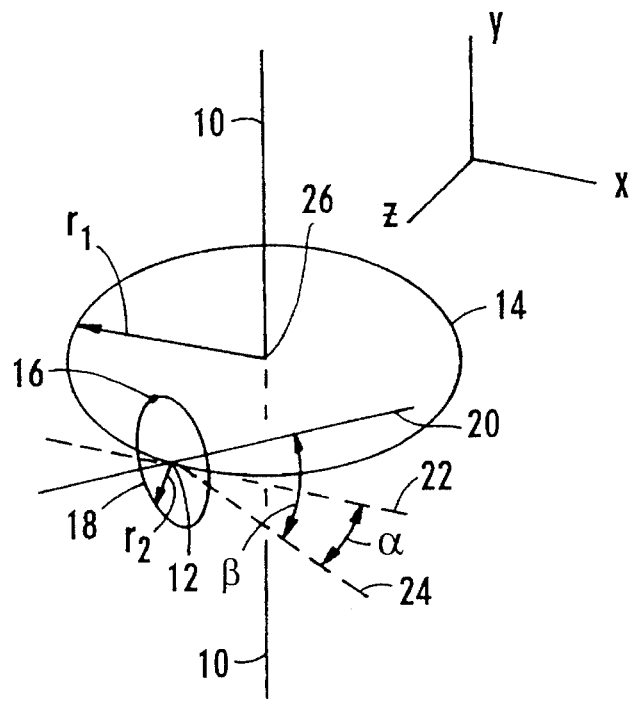
FIG. 1 is an isometric depiction of the geometric considerations for generation of a torus.

To begin, consider FIG. 1 and the geometric relationships depicted which are helpful for a mathematical understanding of the present invention. When initially considering the geometric relationships of FIG. 1, it may be less confusing to not attempt to relate the x—y—z axis systems shown to the conventional anatomical reference planes. This relationship is best made after the geometries involved are established.

In FIG. 1, a first axis 10 is shown arbitrarily directed in the y direction of the x—y—z coordinate system. Consider now a point 12 in the x—y—z system which does not lie on the axis 10. It is clear that, if the point 12 is rotated about the axis 10 at a fixed distance $r_1$ from the axis 10 and in a plane which is perpendicular to the axis 10, the point 12 will follow a circular path 14. For the geometry shown in FIG. 1, the circular path 14 is shown to be in the x—z plane and $r_1$ is the radius of the resultant circle.

Next, consider the rotation of a point 16 around the point 12. Such a rotation will result in a circular path 18, if the point 16 stays at a fixed distance $r_2$ from the point 12 and remains in a plane which is perpendicular to an axis 20 passing through the point 12. For this rotation, $r_2$ is the radius of the resultant circle. The exact orientation of circular path 18 relative to circular path 14 is also important for a complete understanding of the geometry involved with the present invention. To establish this orientation, axis 20 can be described by the off-set angles $\alpha$ and $\beta$. Specifically, the angle $\alpha$ is defined as the angle between a line 22 which lies in the x—z plane tangent to path 14 at point 12 and the projection 24 of axis 20 in the x—z plane. The angle $\beta$ is then defined as the angle between the axis 20 and its projection 24 in the x—z plane.

Figure 2:
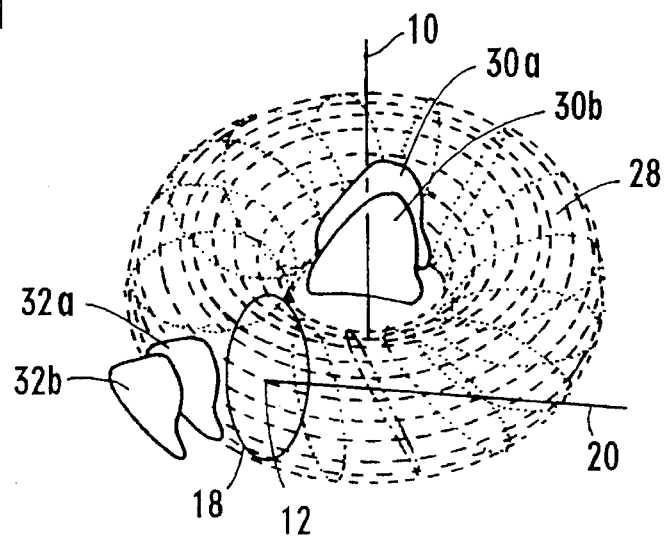
FIG. 2 is an isometric view of a torus with surface portions thereof selected for use as abutting surfaces of the prosthetic replacement joint of the present invention.

By definition, a torus is a solid which is generated by rotating the center of a circle about an external axis. In FIG. 1, the circle is established by the circular path 18 and the external point is the point 26 where axis 10 intersects the x—z plane. Thus, if circular path 18 is rotated around axis 10, along circular path 14, the torus 28 of FIG. 2 is generated. Recognize at this point that the variable geometric parameters involved in generating torus 28 are: i) radius $r_1$, ii) radius $r_2$, iii) angle $\alpha$, and iv) angle $\beta$. For the most trivial case where both of the angles $\alpha$ and $\beta$ are zero degrees, and depending on the values given to $r_1$ and $r_2$, the torus 28 will be doughnut shaped and be either a very thin or a very fat doughnut. It happens, however, that the range of values for both $\alpha$ and $\beta$ are between zero and one hundred and eight degrees (0°–180°). Accordingly, with values give to the angles $\alpha$ and $\beta$, as is normally the case, the torus 28 can be skewed.

Recall the observation previously made that many anatomical joints cause a member to rotate about two axes that are non-perpendicular and non-intersecting. This is the same as the case for the skewed torus 28. The present invention incorporates this notion.

Referring to FIG. 2, a portion of the surface of skewed torus 28 is shown and designated 30a. Along with the surface 30a, a surface 30b is also shown. For purposes of illustration only, the surface 30b is shown to be slightly distanced from the surface 30a. Geometrically, the surfaces 30a and 30b conform, or mate, with each other in the position shown. In effect, surface 30a and 30b have a male-female relationship with each other. Similarly, other portions of the skewed torus 28 are shown as the surfaces 32a and 32b. The surfaces 30a and 30b, however, differ from the surfaces 32a and 32b in their relationships with the first axis of rotation 10 and their respective second axis of rotation 20 (Note: axis 20 is not shown in its position for the surfaces 30a and 30b).

As indicated above, the surfaces of bones which abut each other at a joint are typically surfaces of revolution similar to the surface of skewed torus 28. Accordingly, the surfaces 30a–30b and the surfaces 32a–32b of skewed torus 28, if properly dimensioned, will duplicate or mimic the bone surfaces of anatomical joints.

Figure 3:
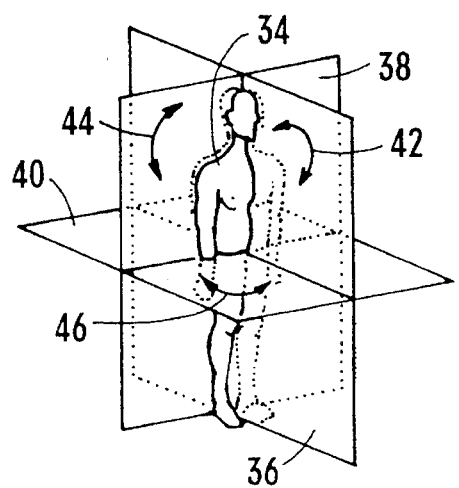
FIG. 3 is an isometric view of a human being shown in relationship to the three anatomical reference planes.

In order to relate the geometry of skewed torus 28 to the human body, consider the generic man 34 shown in FIG. 3. By convention, movements of generic man 34 are referenced to three anatomical planes. These are: the sagittal plane 36, the coronal plane 38, and the transverse plane 40. Depending on the positioning of the reference planes 36, 38 and 40, any movement of generic man 34 can be described as a rotation in one or more of these planes. Specifically, rotations in the sagittal plane 36 are shown by arrow 42 to indicate movements in flexion and extension, rotations in the coronal plane 38 are shown by arrow 44 to indicate movements in abduction and adduction, and rotations in the transverse plane 40 are shown by arrow 46 to indicate external and internal movements.

Now compare FIG. 3 with FIGS. 1 and 2, and, more specifically, consider the movement of point 16 along circular path 18. Also, imagine the x—y—z coordinate system with the y axis aligned on axis 10, and the z axis intersecting point 12. If angles $\alpha$ and $\beta$ have values which are greater than zero, the projection of circular path 18 onto the x—y plane (compare with sagittal plane 36) will indicate some rotation in either flexion or extension. Similarly, the projection of circular path 18 onto the y—z plane (compare with coronal plane 38) will indicate some rotation in either abduction or adduction. Likewise, by projecting circular path 18 onto the x—z plane (compare with transverse plane 40), an internal or external rotation is indicated. Therefore, in accord with the anatomical reference planes 36, 38 and 40 of generic man 34, any movement along the surface of skewed torus 28 is manifested as movements of flexion-extension, abduction-adduction, and external-internal. The consequence of this is that prosthetic joints which have abutting surfaces similar to the surfaces 30a,b or 32a,b can be properly dimensioned to duplicate or mimic the replaced anatomical joint.

Figure 4:
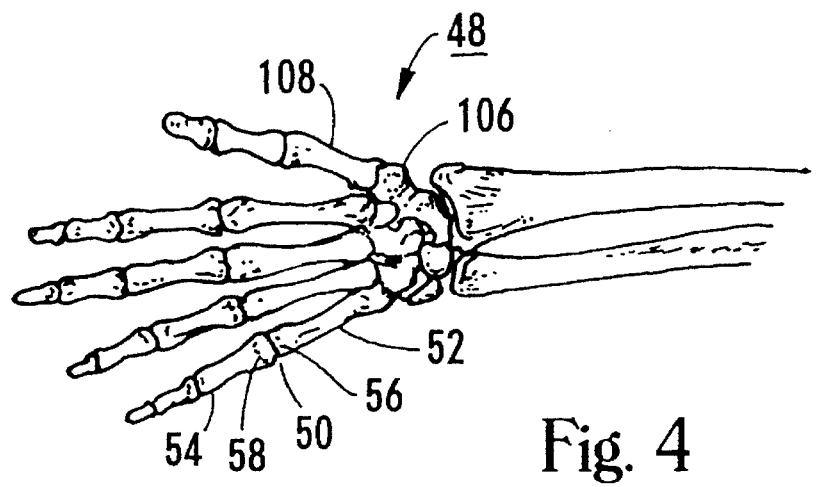
FIG. 4 is a plan view of the skeleton of a hand.

Referring now to FIG. 4 the skeleton of a hand of generic man 34 is shown and generally designated 48. The hand 48 is shown here only for exemplary purposes and it is to be understood that other anatomical structures could as easily be discussed in the context of the present invention. Nevertheless, hand 48 is shown with a finger joint 50 which connects the bone member 52 with the bone member 54. More specifically, a surface 56 of bone member 52 abuts a surface 58 of the bone member 54. Consequently, the bone surfaces 56 and 58 move relative to each other as the bone member 52 is rotated about the finger joint 50. As indicated above, surfaces 56 and 58 will very closely resemble a portion or area on the surface of a skewed torus 28. In accordance with the present invention, if the finger joint 50 needs to be replaced, a prosthetic joint having surfaces 30a–30b or 32a–32b needs to be manufactured.

Recall, many anatomical joints, like finger joint 50, are characterized by two axes of rotation which are non-perpendicular and non-intersecting. Thus, using the geometrical parameters set out in FIG. 1, the joint 50 has a first axis 10 and a second axis 20. It happens that both an axis 10 and an axis 20 can be anatomically identified and located for the finger joint 50. This identification can be accomplished in a manner well known in the art, and will apply for other joints in the skeleton of generic man 34 as well as for the joint 50. Note, having identified axis 10 and axis 20 and their relationship to each other, the off-set angles $\alpha$ and $\beta$ are determined. Also, the intersection between bone surfaces 56 and 58 can be anatomically located for the joint 50 relative to the axes 10 and 20. With the location of the intersection between bone surfaces 56 and 58, the radii $r_1$ and $r_2$ of the skewed torus are established. Consequently, by making simple anatomical measurements of the joint 50, the parameters $\alpha$, $\beta$, $r_1$, and $r_2$ of skewed torus 28 are determined.

Figures 5A, 5B:
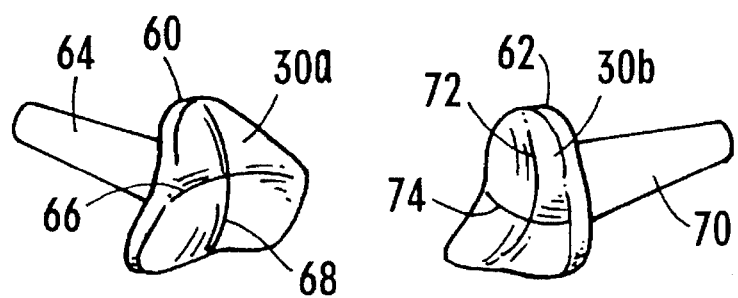
FIGS. 5A and 5B are different angle perspective views of mating surfaces taken from the torus shown in FIG. 2 for use in a prosthetic joint wherein the joint surfaces are between the two axes of rotation which define the torus.

Using anatomical measurements for the parameters $\alpha$, $\beta$, $r_1$, and $r_2$, the surfaces 30a–b or 32a–b can be generated mathematically. This information can then be used to manufacture mating prosthetic members 60 and 62 which are shown respectively in FIGS. 5A and 5B. Referring first to FIG. 5A, the prosthetic member 60 is shown with a bearing surface 30a that has a stem 64 attached thereto. The bearing surface 30a is the same as surface 30a of skewed torus 28 and is characterized by a concavity (indicated by the line 66), and a convexity (indicated by the line 68). Similarly, prosthetic member 62 has an attached stem 70. Also, member 62 has a bearing surface 30b which is the same as the surface 30b of skewed torus 28. As can be appreciated by cross referencing FIG. 5A with 5B, the bearing surface 30b of member 62 has a concavity (indicated by line 72) which conforms to the convexity of bearing surface 30a on member 60. Also, bearing surface 30b of member 62 has a convexity (indicated by line 74) which conforms to the concavity of bearing surface 30a on member 60. Thus, prosthetic members 60 and 62 have mating surfaces.

Figures 6A, 6B:
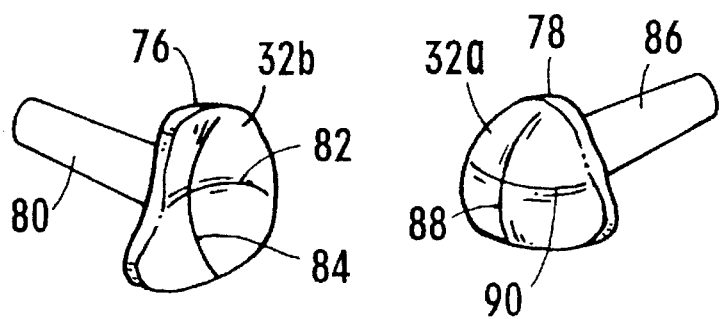
FIGS. 6A and 6B are different angle perspective views of mating surfaces from the torus shown in FIG. 2 for use in a prosthetic joint wherein the joint surfaces are proximal to or distal from the two axes of rotation which define the torus.

As discussed here, the prosthetic members 60 and 62 have bearing surfaces 30a–b which are needed when the abutting surfaces of the anatomical joint being replaced are between the axes 10 and 20. On the other hand, if the abutting surfaces of the anatomical joint which is being replaced are both either proximally or distally located in their relationship to the axes 10 and 20, then a mating pair of prosthetic members having bearing surfaces which are the same as surfaces 32a–b will be required. FIGS. 6A and 6B show such a pair of prosthetic members.

FIGS. 6A and 6B respectively show a prosthetic member 76 having a bearing surface 32b and a prosthetic member 78 having a bearing surface 32a. In FIG. 6A it will be seen that the member 76 includes an attached stem 80 and that the bearing surface 32b is concave, as indicated by the lines 82 and 84. FIG. 6B, shows that prosthetic member 78 includes an attached stem 86 and that the bearing surface 32a is convex, as indicated by the lines 88 and 90. Because the bearing surfaces 32a and 32b conform to each other, they will mate with each other when juxtaposed.

In an operation for the replacement of the finger joint 50 shown in FIG. 4, the rotational axes 10 and 20 are located on the joint 50 to determine the anatomical parameters $\alpha$, $\beta$, $r_1$ and $r_2$. A pair of prosthetic members 60,62 (or 76,68), which have manufactured with dimensions that comply with the anatomical parameters $\alpha$, $\beta$, $r_1$ and $r_2$ are selected. After properly preparing the bones 52 and 54, in a manner well known to orthopedic surgeons, the prosthetic members 60,62 are attached to the bones 52 and 54 to correctly mimic the anatomical structure of the joint being replaced. The original muscles and ligaments associated with joint 50 are then reconnected, if possible, and the prosthetic joint comprising the prosthetic members 60,62 is set. Bones 52 and 54 will then be enabled to move relative to each other in a manner which will duplicate and mimic their natural rotation around two non-perpendicular and non-intersecting axes of rotation.

Figure 7:
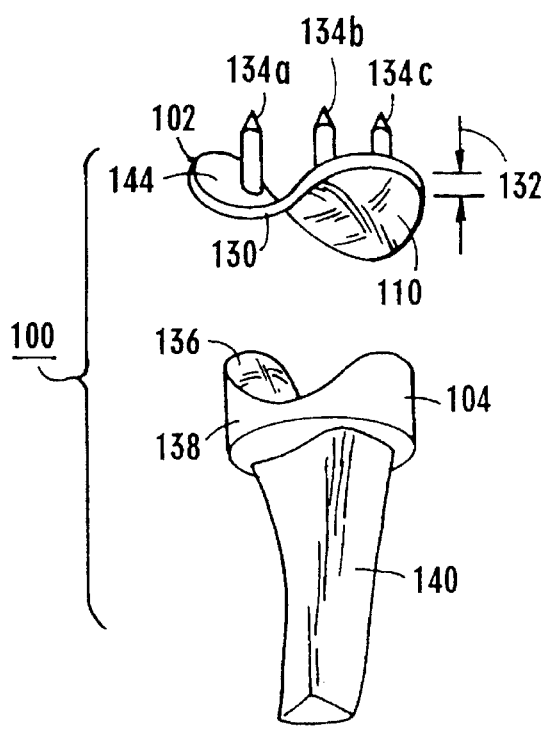
FIG. 7 is a perspective view of the components of the prosthetic carpometacarpal (CMC) thumb joint according to the present invention showing its trapezial member and metacarpal member.
Figure 10:
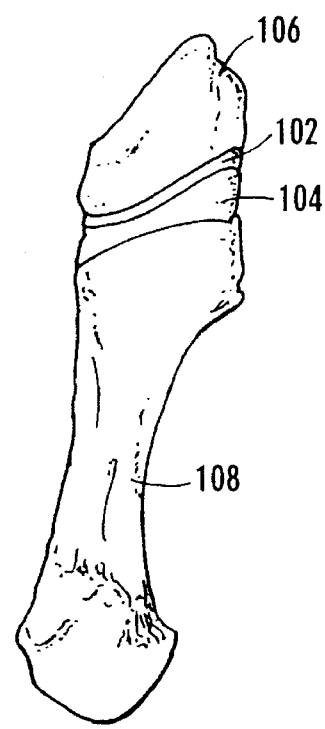
FIG. 10 is a skeletal drawing of the carpometacarpal thumb joint with the replacement prosthetic carpometacarpal joint of the present invention implanted.

In the particular case of the carpometacarpal (CMC) thumb joint, a prosthesis according to the present invention for this joint is shown in FIG. 7 and generally designated 100. As shown in FIG. 7, CMC joint 100 includes a trapezial member 102 and a metacarpal member 104. To appreciate the anatomy which CMC joint 100 is intended to mimic, reference is briefly made back to FIG. 4. It will be seen in FIG. 4 that the thumb of hand 48 includes a trapezium bone 106 and a first metacarpal bone 108. The interface between these bones, the trapezium 106 and the first metacarpal 108, establishes the anatomical CMC joint for the thumb. The members 102 and 104 of prosthetic CMC joint 100 are, therefore, intended to duplicate the interfacing anatomical surfaces of the trapezium 106 and the first metacarpal 108 and mimic the interaction of these two bones with respect to each other.

FIG. 7 shows that trapezial member 102 is formed with an engaging surface 110. Specifically, engaging surface 110 is formed as a surface of revolution about two off-set axes which are not perpendicular to each other and which do not intersect. As indicated above, movement at the carpometacarpal joint of the thumb is characterized by a rotation about two such axes. An anatomical reference for this rotation may be helpful.

Figure 8:
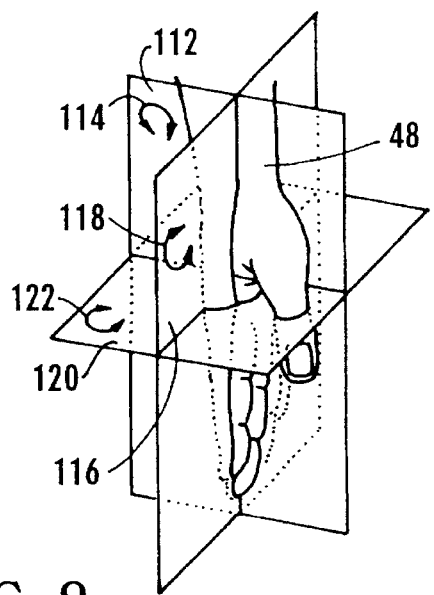
FIG. 8 is an isometric view of a human hand shown in relationship to the three anatomical reference planes.

FIG. 8 shows the anatomical references for the hand 48 in a manner similar to the above-disclosed anatomical references for generic man 34 shown in FIG. 3. Specifically, movements of hand 48, to include the thumb, are typically described with reference to rotations in three mutually perpendicular planes which are related to the hand 48 as shown in FIG. 8. These are: i) the sagittal plane 112 in which rotations in extension and flexion occur as shown by arrow 114; ii) the coronal plane 116 in which rotations in abduction and adduction occur as shown by arrow 118; and iii) the transverse plane 120 in which internal and external rotations occur as shown by arrow 122.

Figure 9:
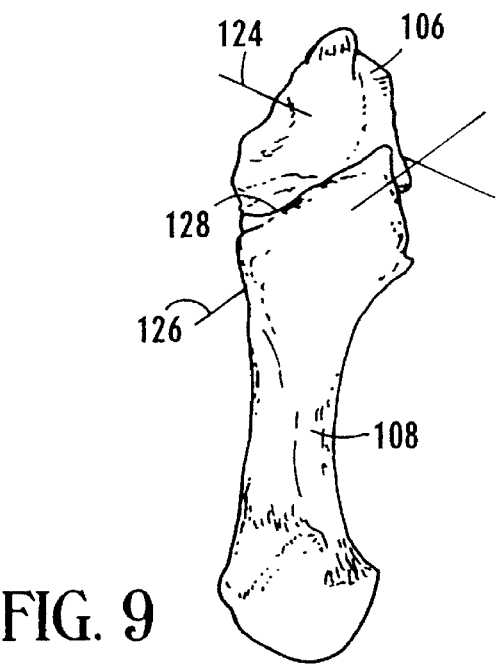
FIG. 9 is an anatomical skeletal drawing of the carpometacarpal thumb joint.

It has been implicitly stated above that a movement at the carpometacarpal joint of the thumb is characterized by a mutual rotation about two off-set axes which are particular for the CMC joint. The actual location of these axes can be determined by means well known in the pertinent art and found to be generally established in relation to the joint as shown in FIG. 9. Specifically, FIG. 9 shows a first axis of rotation 124 which is located on the trapezium bone 106, and a second axis of rotation 126 which is located on the first metacarpal bone 108. Consequently, movement at the interface 128 between trapezium 106 and first metacarpal 108 will be along a surface of revolution about both of the axes 124 and 126. In any event, the result is an anatomical movement of the thumb about the CMC joint which involves rotations in all three anatomical planes, the sagittal plane 112, the coronal plane 116 and the transverse plane 120.

In general, the first axis of rotation 124 on trapezium 106 is referred to as an axis of flexion and extension. Similarly, the second axis of rotation 126 on first metacarpal bone 108 is referred to as an axis of abduction and adduction. These generalizations, however, are not quite anatomically true since neither of the axes 124 and 126 are perpendicular to any of the anatomical reference planes 112, 116 and 120. Therefore, combinations of rotations in more than one anatomical reference plane may be experienced during movement of the thumb. In relation to each other, and using notation previously disclosed with reference to FIG. 1, it has been established that there are two off-set angles, α and β, between axis 124 and axis 126. For the CMC joint, the first off-set angle (α) is in the range of 11.7°±20°, and the second off-set angle (β) is in the range of 17.3°±17.3°, with typical values being respectively 11.7° for α and 17.3° for β.

Returning now to FIG. 7 it will be seen that the engaging surface 110 of trapezial member 102 is formed on a base 130. While the distance 132 representing the thickness of base 130 can be varied somewhat, the distance 132 is preferably such that base 130 is relatively thin. The desire to minimize distance 132 is mentioned here to emphasize that trapezial member 102 is intended to be a surface replacement for the anatomical surface of trapezium 106 at the interface 128. FIG. 7 also shows that pegs 134a, 134b and 134c extend from a surface which is on the side of base 130 that is opposite the engaging surface 110. The pegs 134 are substantially parallel to each other and are arranged on the base 130 in a configuration which provides for stabilized fixation of the trapezial member 102 on the trapezium 106 and for minimal interactive stresses between the member 102 and the trapezium 106 during movement of the thumb.

For the present invention, the underside of base 130 of trapezial member 102 is preferably a saddle-shaped surface 144 which may, and most often will, have a slightly different configuration than the engaging surface 110. Thus, the distance 132 through the base 130 will not be uniform. More specifically, it is preferable that the surface 144, unlike engaging surface 110, be generated as a surface of revolution about orthogonal axes (not shown). Such a configuration for surface 144 simplifies preparation of the surface of the trapezium 106, which can then also be shaped as a surface of revolution about orthogonal axes. This will facilitate engagement of the trapezium 106 with surface 144 of trapezial member 102. Further, the particular configuration for saddle-shape surface 144 for trapezial member 102, and the consequent variations in distance 132 for the depth of base 130 between saddle-shaped surface 144 and the engaging surface 110, can be tailored to effectively place load distributions across the engaging surface 110 to reduce undesirable torsional and shear forces between the trapezial member 102 and the trapezium 106.

Also shown in FIG. 7 is an embodiment of the metacarpal member 104 of prosthetic CMC joint 100 according to the present invention. As shown, metacarpal member 104 includes an engaging surface 136 which is formed on a base 138, and it has a stem 140 which extends from the base 138 in a direction generally away from the engaging surface 136. For purposes of the present invention, the engaging surface 136 of metacarpal member 104 is formed to join in a mating engagement with the engaging surface 110 of trapezial member 102 when the two members 102 and 104 are operationally juxtaposed. As also shown in FIG. 7, the stem 140 has a generally triangular cross-section which helps stabilize the member 104 in rotation after the member 104 has been attached to the first metacarpal bone 108.

Figure 11:
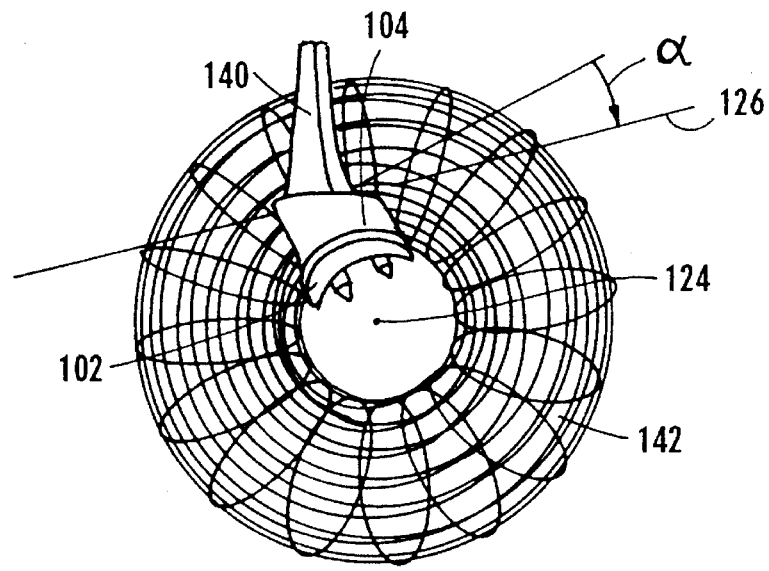
FIG. 11 is a plan view of a torus with a trapezial member and a metacarpal member of the joint superposed on the same surface portion of the torus.

To geometrically illustrate the mating engagement of trapezial member 102 with metacarpal member 104, reference is made to FIG. 11. FIG. 11 shows a plan view of a torus 142 having a surface of revolution generated by rotations about both the (F-E) axis 124 which is oriented on the trapezium 106, and the (Ab-Ad) axis 126 which is oriented on the metacarpal bone 108. Due to the fact FIG. 11 is a plan view of the torus 142, in accordance with standard requirements for illustration, the angle β can not be shown in FIG.

11 and the axis 124 is shown as a dot. Nevertheless, both the trapezial member 102 and the metacarpal member 104 of CMC joint 100 are shown in mating engagement and, to show their relationship with the torus 142, both members 102 and 104 are superposed on the same portion of the surface of torus 142.

In order to attach CMC joint 100 of the present invention between trapezium 106 and metacarpal 108 to replace a diseased or damaged joint, the trapezium 106 and the first metacarpal bone 108 must first be prepared. This is done for the trapezium 106 by a resurfacing arthroplasty which involves removal of as little bone as possible from the trapezium 106. Thus, preferably, only the osteophytes, cartilage and a small amount of bone are removed to allow for an intimate fit between the trapezium 106 and the trapezial member 102. Once, the trapezium is thus prepared, the trapezial member 102 can then be press-fit into the trapezium. To do this, the trapezial member 102 is properly oriented on the trapezium 106 with pegs 134 positioned against the bone. The trapezial member 102 is then pressed against the trapezium 106 to embed the pegs 134 a, b and c into the bone. Cement fixation should be required in only a minority of cases, such as those with poor bone quality or large defects. This should reduce failures and bone loss attributable to cement factors.

Attachment of the metacarpal member 104 to the first metacarpal bone 108 is accomplished slightly differently than described above for attachment of the trapezial member 102 to the trapezium 106. In the case of the first metacarpal bone 108, the proximal canal of the bone 108 is cleared to receive the stem 140 of metacarpal member 104. Due to the anatomical shape of the proximal metacarpal canal, the stem 104 can be slightly bent to correspond to this shape in order to provide a snug interference fit therewith. Further, in order to provide greater stability against rotation of the member 104, the stem 140 preferably has a generally triangular cross-section. Similar to the attachment of trapezial member 102 to the trapezium 106, the metacarpal member 104 can be press fit against the first metacarpal bone 108. This is done simply by inserting the stem 140 of metacarpal member 104 into the proximal metacarpal canal of bone 108 and pressing the member 104 into place. Similarly, as for the trapezial member, it is preferable if the metacarpal member can be press-fit into the first metacarpal bone 108 without the use of a cement. As indicated above, however, there may be cases where the use of cement may be required.

Importantly, metacarpal member 104 must be attached or anchored into first metacarpal bone 108 with an orientation which allows for its mating engagement with trapezial member 102. Further, the orientations of both trapezial member 102 and metacarpal member 104 on their respective bones must be such that mutual rotations around both axes 124 and 126 are realized during movement of the thumb.

Figure 12:
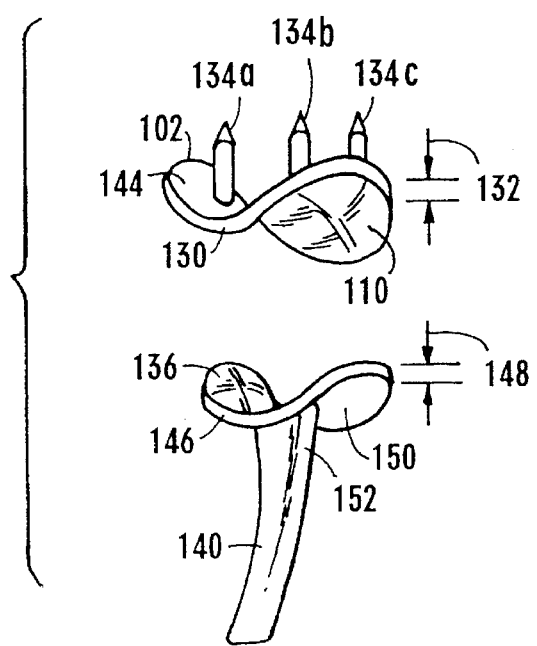
FIG. 12 is an isometric view of the CMC joint of the present invention with an alternate embodiment of the metacarpal member.

FIG. 12 shows an alternate embodiment for the metacarpal member of CMC joint 100 which is identified with the numeral 152. In many respects, the base 146 of metacarpal member 152 is similar to the base 130 of trapezial member 102. Specifically, the base 146 is relatively thin, as indicated by the distance 148. Also, like saddle-surface 144 of trapezial member 102, the underside of base 146 is a saddle-shaped surface 150 which conforms to a surface of revolution about two orthogonal axes (not shown). This is done, as for trapezium 106, to facilitate the required resurfacing of first metacarpal bone 108 for conformance in the engagement of metacarpal member 152 with bone 108. Also, as indicated above for trapezial member 102, the particular configuration for saddle-shape surface 150 of metacarpal member 152, and the consequent variations in distance 148 for changes in the depth of base 146, can be tailored to effectively place load distributions across the engaging surface 136 of metacarpal member 152 to reduce undesirable torsional and shear forces between the member 152 and the first metacarpal bone 108. Thus, like trapezial member 102, the metacarpal member 152, becomes a resurfacing member.

For the present invention, both the trapezial member 102 and the metacarpal member 104, or its alternate embodiment 152, can be made of a number of different type materials or composites of these materials. These materials include but are not limited to: i) metals, such as CoCr Alloys, Titanium and Titanium Alloys and Stainless Steels, ii) plastic, such as Ultrahigh Molecular Weight Polyethylene (UHMWPe), and iii) ceramics, such as Zirconium Oxides (Toughened), Alumina Oxides, Alumin-Zirconia Alloys and Calcium Phosphates. Further, surface enhancements can be used for the metals, plastic, or ceramics. Specifically, for metal surface enhancements, several treatments known in the art can be used. These include but are not limited to: nitrogen ion implantation, plasma nitriding, titanium nitride coating, and pulsfusion surface enhancement bonding of metallics or ceramics to the surfaces.

It has been determined that UHMWPe in conjunction with another material, such as a titanium alloy, is particularly effective for preventing "cold flow". "Cold Flow" which is the permanent or nonrecoverable strain of a material below the yield point in response to continuous high loading in compression or shear, is a particular problem for a joint prosthesis, such as CMC joint 100, which will be subjected only to continuous compression and sheer loading. It has been determined that when using ultra high molecular weight polyethylene materials for the engaging surfaces 110 and 136 of CMC joint 100, use of a metal saddle shape reinforcement, which is similar to the articular surface shape, is one way to prevent cold flow.

While the particular prosthesis for the carpometacarpal joint of the thumb, and its method of manufacture, as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A prosthesis for a carpometacarpal joint of a thumb which comprises:

a trapezial member having a first surface and a second surface, said first surface being a surface of revolution relative to both a first axis and a second axis, said first and second axes being anatomical axes defining the pivoting of a first metacarpal bone of said thumb relative to a trapezium bone of said thumb;

a plurality of pegs mounted on said second surface of said trapezial member for engagement with said trapezium bone, to anchor said trapezial member thereon;

a metacarpal member for abutment with said trapezial member, said metacarpal member having a first surface cooperating with said first surface of said trapezial member;

a stem attached to said metacarpal member, said stem being dimensioned for insertion into a proximal metacarpal canal of said first metacarpal bone of said thumb to anchor said metacarpal member thereon;

wherein said first surface of said trapezial member and said first surface of said metacarpal member match a selected portion of a surface of a reference toroid, said reference toroid being mathematically generated by rotating said second axis about said first axis, while rotating a reference point about said second axis, the orbital radius of said reference point being determined by measuring the location, relative to said first and second axes, of anatomical abutment surfaces between said trapezium bone and said first metacarpal bone, and wherein said first axis passes through said trapezium, a naturally occurring location of sad first axis being determined with an axis finder, and said second axis passes through said first metacarpal bone, a naturally occurring location of said second axis being determined with an axis finder, said second axis being in a fixed relationship with said first axis, and further wherein said first axis and said second axis are non-parallel, non-perpendicular and non-intersecting, and the relationship between said first axis and said second axis is characterized by:

(a) a compound angle between said axes, measured at a reference plane perpendicular to said first axis, said compound angle consisting of a first angle ($\alpha$) between the projection of said second axis in said reference plane and a line tangent to the reference plane orbit of said second axis about said first axis, and a second angle ($\beta$) between said second axis and said reference plane; and (b) an orbital distance between said two axes in said reference plane.

2. A prosthesis as recited in claim 1 wherein said first angle ($\alpha$) is in a range of approximately 11.7°±20°, and said second angle ($\beta$) is in a range of approximately 17.3°±17.3°.

3. A prosthesis as recited in claim 1 wherein said pegs are substantially parallel to each other.

4. A prosthesis as recited in claim 1 wherein said stem has a generally triangular cross-section.

5. A prosthesis as recited in claim 1 wherein said trapezial member is made with cobalt chrome and said metacarpal member is made with a composite material comprising titanium and polyethylene.

6. A prosthesis as recited in claim 1 wherein said trapezial member is configured to be press-fit into the trapezium and the metacarpal member is configured to be press-fit into the first metacarpal bone.

7. A prosthesis for a carpometacarpal joint of a thumb which comprises:

a first means attachable to a trapezium bone of said thumb, said first means having an abutment surface formed as a surface of revolution relative to both a first axis and a second axis to substantially duplicate a portion of the anatomical abutment surface between a first metacarpal bone of said thumb and said trapezium bone, said first and second axes being anatomical axes defining the pivoting of said first metacarpal bone relative to said trapezium bone; and a second means attachable to said first metacarpal bone of said thumb and abuttable with said first means, said second means having an abutment surface dimensioned for cooperating abutment with said abutment surface of said first means;

wherein said abutment surface of said first means and said abutment surface of said second means match a selected portion of a surface of a reference toroid, said reference toroid being mathematically generated by rotating said second axis about said first axis, while rotating a reference point about said second axis, the orbital radius of said reference point being determined by measuring the location, relative to said first and second axes, of said anatomical abutment surface between said first metacarpal bone and said trapezium bone; and wherein said first axis passes through said trapezium, a naturally occurring location of said first axis being determined with an axis finder, and said second axis passes through said first metacarpal bone, a naturally occurring location of said second axis being determined with an axis finder, said second axis being in a fixed relationship with said first axis wherein said first axis and said second axis are non-parallel, non-perpendicular and non-intersecting, and the relationship between said first axis and said second axis is characterized by a first angle ($\alpha$) in a first reference plane perpendicular to said first axis, a second off-set angle ($\beta$) in a second reference plane perpendicular to said first reference plane, and a distance between said two axes in said first reference plane.

8. A prosthesis as recited in claim 7 further comprising a plurality of pegs mounted on first means for engaging said first means with the trapezium bone to anchor said first means thereon.

9. A prosthesis as recited in claim 8 further comprising a stem attached to said second means, said stem being dimensioned for insertion into the proximal metacarpal canal of the first metacarpal bone to anchor said second means thereon.

10. A prosthesis as recited in claim 9 wherein said first angle ($\alpha$) is in a range of approximately 11.7°±20°, and said second angle ($\beta$) is in a range of approximately 17.3°±17.3°.

11. A prosthesis as recited in claim 10 wherein said pegs are substantially parallel to each other and said stem has a generally triangular cross-section.

12. A prosthesis as recited in claim 7 wherein said first means is made with cobalt chrome and said second means is made with a composite material comprising titanium and polyethylene.

13. A prosthesis as recited in claim 12 wherein said second means is formed with a titanium portion shaped as said engaging surface and said polyethylene covers said titanium portion to establish said engaging surface.

\* \* \* \* \*